US00PP17789P2

(12) United States Plant Patent
Gitzels

(10) Patent No.: US PP17,789 P2
(45) Date of Patent: Jun. 5, 2007

(54) ***DAHLIA* PLANT NAMED 'DAPASUJE'**

(50) Latin Name: *Dahlia variabilis*
Varietal Denomination: Dapasuje

(75) Inventor: Jeroen Gitzels, Zwaag (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/319,312

(22) Filed: Dec. 28, 2005

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
*Assistant Examiner*—Annette H Para
(74) *Attorney, Agent, or Firm*—Audrey Charles

(57) ABSTRACT

A new and distinct cultivar of *Dahlia* plant named 'Dapasuje' characterized by its dark red and orange-bicolored flowers, medium green-colored foliage, good basal branching character, and moderately vigorous, upright growth habit.

1 Drawing Sheet

Latin name of genus and species of plant claimed: *Dahlia variabilis*.
Variety denomination: 'Dapasuje'.

BACKGROUND OF THE INVENTION

The present invention relates to a new and distinct cultivar of *Dahlia* plant botanically known as *Dahlia variabilis* and hereinafter referred to by the cultivar name 'Dapasuje'.

The new cultivar originated in a controlled breeding program in Rijsenhout, the Netherlands during May 2000. The objective of the breeding program was the development of freely flowering *Dahlia* cultivars with large flowers and a moderately vigorous growth habit.

The new cultivar is a naturally occurring sport of Figaro™ Orange Shades, an unprotected seed propagated variety, characterized by its orange-colored flowers, medium green-colored foliage, and moderately vigorous, upright growth habit. The new cultivar was discovered and selected by the inventor on May 1, 2000 in a controlled environment at Rijsenhout, the Netherlands.

Asexual reproduction of the new cultivar by terminal stem cuttings since May 2000 at Rijsenhout, the Netherlands and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Dapasuje' as a new and distinct cultivar of *Dahlia* plant:

1. Dark red and orange-bicolored flowers;
2. Medium green-colored foliage;
3. Good basal branching character; and
4. Moderately vigorous, upright growth habit.

Plants of the new cultivar differ from plants of the parent primarily in flower color.

Of the many commercially available *Dahlia* cultivars known to the inventor, the most similar in comparison to the new cultivar is 'Dapared', U.S. Plant Pat. No. 17,143. However, in side by side comparisons, plants of the new cultivar differ from plants of 'Dapared' in the following characteristics:

1. Plants of the new cultivar are taller than plants of 'Dapared';
2. Plants of the new cultivar are wider than plants of 'Dapared'; and
3. Plants of the new cultivar have a different flower color from plants of 'Dapared'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Dapasuje'. The plants were grown in 10 cm pots for 8 weeks in a greenhouse at West Chicago, Ill.

DETAILED BOTANICAL DESCRIPTION

Figure 1:
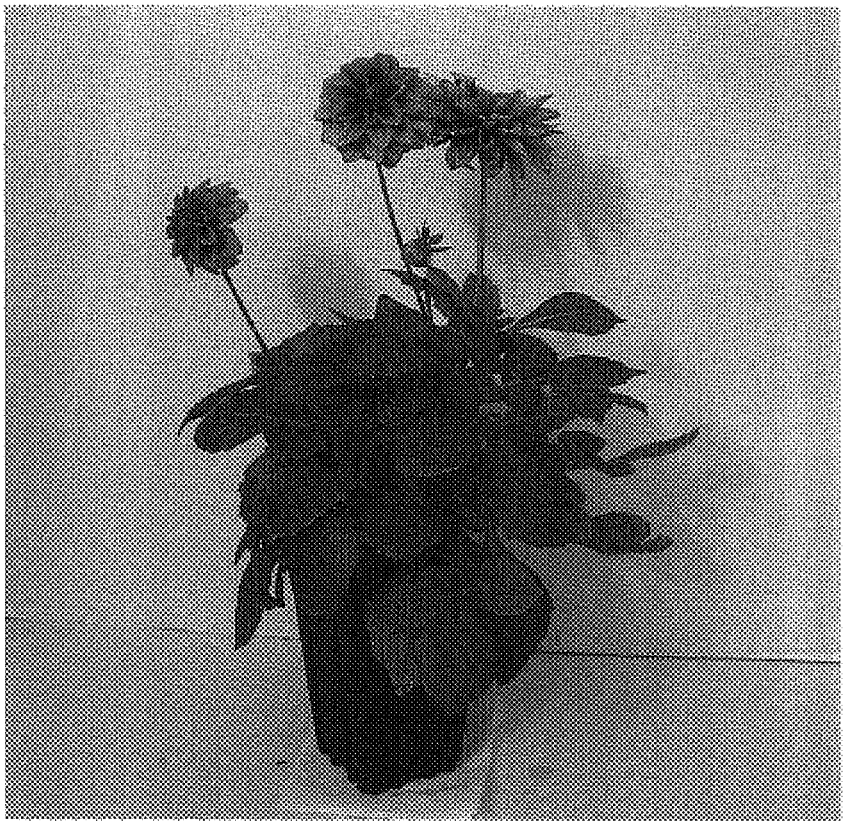
FIG. 1 illustrates a side view of the overall growth and flowering habit of 'Dapasuje'.
Figure 2:
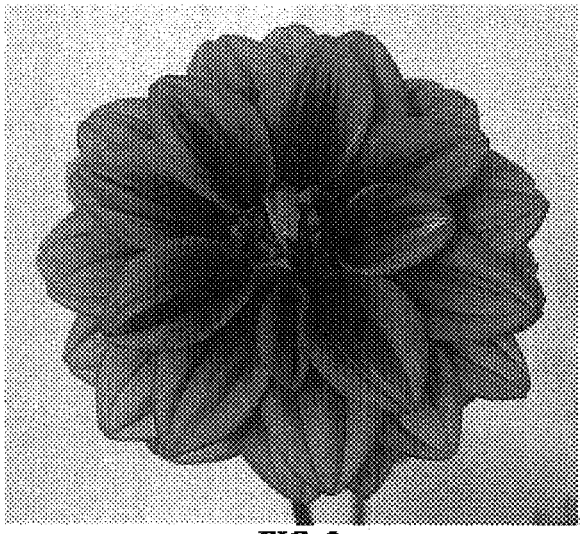
FIG. 2 illustrates a close-up view of a single inflorescence of 'Dapasuje' with most of the ray florets open and the disc florets unopened.
Figure 3:
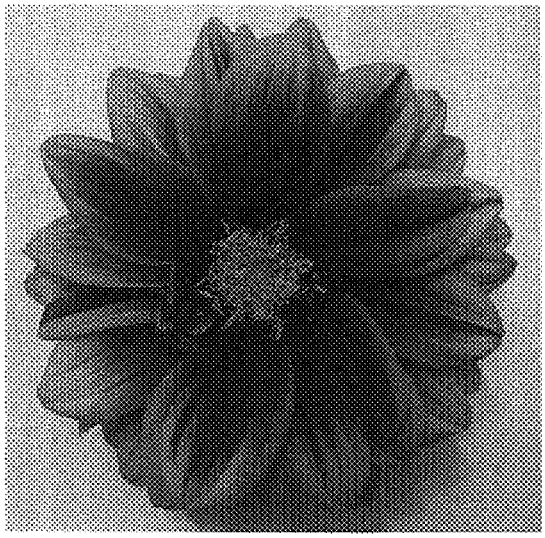
FIG. 3 illustrates a close-up view of the ventral surface of an inflorescence of 'Dapasuje' with fully open ray florets and fully open disc florets.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Dec. 16, 2005 between 1:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 8 weeks utilizing a soilless growth medium. Greenhouse temperatures were maintained at approximately 65° F. to 75° F. (18° C. to 24° C.) during the day and approximately 60° F. to 65° F. (15° C. to 18° C.) during the night. Greenhouse light levels of approximately 4,000 to 6,000 footcandles were maintained during the day.

Botanical classification: *Dahlia variabilis* cultivar Dapasuje.

Parentage:

*Parent.*—*Dahlia variabilis* cultivar Figaro™ Orange Shades, an unprotected seed propagated variety.

Propagation:

*Type cutting.*—Terminal stem.

*Time to initiate roots.*—Approximately 7 to 10 days.

*Time to produce a rooted cutting.*—Approximately 21 to 28 days.

*Root description.*—Fine, fibrous.

*Rooting habit.*—Freely branching.

*Tuber formation.*—Will form under short day conditions of at least 13 to 14 hours of darkness.

Plant description:

*Crop time.*—Approximately 6 to 8 weeks from a rooted cutting.

*Growth habit.*—Basal branching; pinching enhances branching.

*General appearance.*—Moderately vigorous, upright.

*Size.*—Height from soil level to top of plant plane: Approximately 27.2 cm. Height from soil level to top of foliage: Approximately 19.3 cm. Width: Approximately 31.8 cm.

*Branch.*—Quantity per plant: 2. Strength: Strong. Length: Approximately 10.2 cm. Diameter: Approximately 9.3 mm. Texture: Glabrous. Color: 144A. Length of central internode: Approximately 8.4 mm.

*Foliage.*—Quantity of leaves per lateral branch: Approximately 14. Type: Simple and compound leaves. Quantity of leaflets per compound leaf: Approximately 3 to 5. Fragrance: None. Arrangement: Opposite. Aspect: Petiole is at an acute angle to stem and mature blade is perpendicular to stem. Shape of leaf and leaflet: Ovate. Margin of leaf and leaflet: Widely dentate. Apex of leaf and leaflet: Acuminate. Base of leaf and leaflet: Acuminate. Venation pattern: Pinnate.

*Simple leaf.*—Length: Approximately 9.9 cm. Width: Approximately 5.0 cm. Texture of upper and lower surfaces: Sparsely pubescent with denser pubescence along veins. Color of upper surface: Closest to 137A with venation of 144A. Color of lower surface: 191B with venation of 144A. Length of petiole: Approximately 3.3 cm. Diameter of petiole: Approximately 3.3 mm. Texture of upper and lower surfaces of petiole: Glabrous. Color of upper and lower surfaces of petiole: 144A.

*Mature compound leaf.*—Length of mature compound leaf: Approximately 15.8 cm. Width of mature compound leaf: Approximately 12.6 cm. Length of terminal leaflet: Approximately 7.6 cm. Width of terminal leaflet: Approximately 4.8 cm. Length of lateral leaflet: Approximately 6.2 cm. Width of lateral leaflet: Approximately 4.0 cm. Texture of upper and lower surfaces: Sparsely pubescent with denser pubescence along veins. Color of upper surface: Closest to 137A with venation of 144A. Color of lower surface: 191B with venation of 144A. Length of petiole of mature compound leaf: Approximately 4.4 cm. Diameter of petiole of mature compound leaf: Approximately 4.5 mm. Texture of upper and lower surfaces of petiole of mature compound leaf: Glabrous. Color of upper surface of petiole of mature compound leaf: 144A with sparse overlay of 187B near base. Color of lower surface of petiole of mature compound leaf: 144A. Length of rachis: Approximately 3.0 cm. Diameter of rachis: Approximately 2.8 mm. Texture of upper surface of rachis: Sparsely pubescent. Texture of lower surface of rachis: Glabrous. Color of upper surface of rachis: 144A with sparse overlay of 187B near leaflet attachment. Color of lower surface of rachis: 144A.

Flowering description:

*Flowering habit.*—'Dapasuje' is freely flowering under outdoor growing conditions with substantially continuous blooming from spring through autumn and year round in the greenhouse environment.

*Time to first flower.*—Approximately 14 weeks from sticking of unrooted cutting.

*Lastingness of individual bloom.*—Approximately 4 weeks.

Inflorescence description:

*Appearance.*—Type: Composite. Aspect: Facing outward. Flower arrangement: Terminal, arising from leaf axils on strong peduncles positioned over the foliage. Disc and ray florets arranged acropetally on a capitulum. Persistent.

*Quantity per plant.*—3.

*Fragrance.*—None.

*Shape/size.*—Hemispherical when ray florets are fully open. Inflorescence diameter: Approximately 9.5 cm. Inflorescence depth: Approximately 5.0 cm. Disc diameter: Approximately 8.5 mm. Receptacle diameter: Approximately 1.1 cm. Receptacle depth: Approximately 3.8 mm. Receptacle color: Between 150B and 150C.

*Peduncle.*—Strength: Strong. Aspect: Erect. Length: Approximately 13.7 cm. Diameter: Approximately 3.0 mm. Texture: Glabrous. Color: 144A with an overlay of 187B.

*Bud.*—Rate of bud opening: Generally takes approximately 2 weeks for bud to progress from first color to fully open inflorescence. Shape: Oval. Depth at first color: Approximately 1.9 cm. Diameter at first color: Approximately 1.8 cm. Texture at first color: Glabrous. Color: Outer surface of bract is 144C with 137B at base, petal background is 167B with central stripes of 182A and base of N144C.

*Ray florets.*—Quantity per inflorescence: Approximately 62. Arrangement: Imbricate, in several whorls. Aspect: Cupped. Shape: Oblanceolate. Margin: Entire. Apex: Acute. Base: Attenuate. Appearance: Dull. Length: Approximately 4.4 cm. Width: Approximately 2.0 cm. Texture of upper and lower surfaces: Glabrous. Color of upper surface when first open: 59A at base transitioning to 45B with varying amounts of 167C on outer edges near apex and apex. Color of lower surface when first open: 167D with streaks of 182A. Color of upper surface when fully open: 59A at base transitioning to 45B towards apex with varying amounts of 167C on outer edges and apex. Color of lower surface when fully open: 163C with streaks of 182A. Color of upper surface before senescence: 59A at base transitioning to 164A at apex. Color of lower surface before senescence: 198C at base transitioning through 59A to 164A at apex.

*Disc florets.*—Quantity per inflorescence: Approximately 36. Arrangement: Massed in center of inflorescence. Aspect: Erect. Shape: Tubular. Margin: Entire. Apex: 5 acute down turning tips. Base: Fused. Length: Approximately 9.4 mm. Diameter at apex: Approximately 2.4 mm. Diameter at base: Approximately 1.0 mm. Texture: Glabrous. Color when fully open: N144C with varying amounts of 59A, translucent.

*Outer involucral bracts.*—Quantity: 7. Aspect: Flat. Shape: Rhombic. Margin: Entire. Apex: Acute. Base: Truncate. Length: Approximately 1.4 cm. Width: Approximately 8.0 mm. Texture of upper and lower surfaces: Glabrous. Color of upper and lower surfaces: 138A.

*Inner involucral bracts.*—Quantity: One per floret. Shape: Linear, slightly overlapping. Margin: Entire. Apex: Broadly acute. Base: Truncate. Length of outermost: Approximately 1.6 cm. Width of outermost: Approximately 6.0 mm. Length of innermost: Approximately 8.2 mm. Width of innermost: Approximately 2.6 mm. Texture of upper and lower surfaces: Glabrous. Color of upper and lower surfaces: 150B, translucent with a base of 137A for outermost.

*Reproductive organs.*—Androecium: On disc florets. Stamen quantity: 5. Anther shape: Linear. Anther length: Approximately 4.0 mm. Anther color: 13A. Pollen amount: Abundant. Pollen color: 16A. Gynoecium: On disc and ray florets. Pistil length: Approximately 7.5 mm. Stigma shape: 2 to 3 branches. Stigma length: Approximately 2.9 mm. Stigma color: 13A. Style length: Approximately 5.5 mm. Style color: 1D, transparent. Ovary diameter: Approximately 1.0 mm. Ovary color: 1D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Dapasuje', substantially as herein shown and described.

* * * * *